(12) United States Patent
Kempenich

(10) Patent No.: US 12,285,632 B2
(45) Date of Patent: Apr. 29, 2025

(54) FIXED-POINT MAMMALIAN SPINE-LIKE APPARATUS THAT PROVIDES AN ACCURATE AND FIXED ALIGNMENT POINT OF REFERENCE FOR PRE-TREATMENT CT WHILE PHANTOM AND RADIATION DETECTORS OF A DYNAMIC RADIATION ONCOLOGICAL PHANTOM SYSTEM ARE IN MOTION AND A TUMOR TRACKING BLOCK WITH A TARGET OBJECT OF VARIABLE SIZE, SHAPE, AND DENSITY AND METAL FIDUCIAL MARKERS USED TO MARK TUMORS IN HUMAN TREATMENT

(71) Applicant: Aaron Anthony Kempenich, Grand Forks, ND (US)

(72) Inventor: Aaron Anthony Kempenich, Grand Forks, ND (US)

( * ) Notice: Subject to any disclaimer, the term of this patent is extended or adjusted under 35 U.S.C. 154(b) by 0 days.

(21) Appl. No.: 18/635,926

(22) Filed: Apr. 15, 2024

(65) Prior Publication Data
US 2024/0342506 A1 Oct. 17, 2024

Related U.S. Application Data

(60) Provisional application No. 63/459,164, filed on Apr. 13, 2023, provisional application No. 63/459,181, filed on Apr. 13, 2023.

(51) Int. Cl.
*A61N 5/10* (2006.01)

(52) U.S. Cl.
CPC ......... *A61N 5/1049* (2013.01); *A61N 5/1071* (2013.01); *A61N 5/1075* (2013.01);
(Continued)

(58) Field of Classification Search
CPC ..... A61B 6/545; A61B 6/4476; A61B 6/4441; A61B 90/36; A61B 6/505; A61B 6/584;
(Continued)

(56) References Cited

U.S. PATENT DOCUMENTS

2005/0152502 A1* 7/2005 Saunders ............... A61B 6/583
378/207
2006/0002519 A1* 1/2006 Jenkins ................ A61N 5/1048
378/207
(Continued)

*Primary Examiner* — Irakli Kiknadze
(74) *Attorney, Agent, or Firm* — Plager Schack LLP; Mark H. Plager, Esq.; Stephen Hallberg, Esq.

(57) ABSTRACT

A fixed-point mammalian spine-like apparatus and a tumor tracking block with a variable size, shape, density target object and metal fiducial markers used to mark tumors in human treatment are disclosed. The tumor tracking block is configured in shape and size to fit into a dock of a dynamic radiation oncological phantom system with the target tracked in coordination with a linear accelerator. The fixed-point mammalian spine-like apparatus provides an accurate and fixed alignment point of reference for pre-treatment dose delivery evaluation the target is in motion. The fixed-point mammalian spine-like apparatus includes a connector that attaches to a frame of the phantom system, ensuring that the alignment point of reference of planning CT data to pre-treatment CT (kV or MV) is proper and accurate, while allowing the phantom with its detectors to be in motion, realistically representing a human under treatment.

8 Claims, 10 Drawing Sheets

(52) U.S. Cl.
CPC ............... *A61N 2005/1051* (2013.01); *A61N 2005/1076* (2013.01)

(58) Field of Classification Search
CPC ......... A61B 6/027; A61B 6/025; A61B 6/032; A61B 6/583; A61B 6/469; A61B 2090/3966; A61B 2090/376; A61B 2034/2059; A61B 2017/00712; A61B 2090/367; A61B 5/4509; A61B 5/748; A61B 6/4423; A61B 6/482; A61B 18/1492; A61B 8/0883; A61B 8/445; A61B 8/4477; A61B 8/4494; A61B 8/461; A61B 8/12; A61B 5/055; A61B 6/5247; A61B 5/416; A61B 6/03; A61B 5/0044; A61B 90/39; A61B 6/4266; A61B 2090/3937; A61B 6/54; A61B 6/0407; A61B 5/1127; A61B 6/0421; A61B 90/14; A61B 2090/101; A61B 2562/0252; A61B 5/0036; A61B 5/1113; A61B 6/037; A61B 6/0478; A61B 6/487; A61B 6/582; A61B 2560/0228; G06T 7/11; G06T 7/0012; G09B 23/30; G09B 23/286; G09B 23/28; A61N 5/104; A61N 5/1071; A61N 5/1075; A61N 2005/1051; A61N 2005/1076; A61N 1/0587; A61N 5/1067; A61N 5/1049; A61N 2005/1061; A61N 5/1077; A61N 5/1045; A61N 2005/1054; A61N 5/1081; A61N 5/10; A61N 5/1001; A61N 5/1078; A61N 2005/1074; A61N 2005/1087; A61N 2005/105; A61N 2005/1055; A61N 2005/1059; A61N 2005/1052; A61N 2005/1058; A61N 5/1048; A61N 2005/1057; A61M 25/0662; A61M 25/0133; A61M 25/0147; G01S 15/8952; G01S 7/52085; G01T 1/2023; G01T 1/2018
USPC ...................................................... 378/18, 65
See application file for complete search history.

(56) References Cited

U.S. PATENT DOCUMENTS

| | | | |
|---|---|---|---|
| 2007/0071176 A1* | 3/2007 | Main ................... | A61N 5/1075 378/207 |
| 2010/0167251 A1* | 7/2010 | Boutchko .............. | A61B 5/055 434/267 |
| 2011/0305380 A1* | 12/2011 | Bose ................... | A61N 5/1075 382/132 |
| 2015/0085993 A1* | 3/2015 | Scheib ................. | A61N 5/1071 378/207 |
| 2016/0114190 A1* | 4/2016 | Brown .................. | A61B 6/584 378/205 |
| 2020/0114173 A1* | 4/2020 | Little .................... | A61B 90/39 |
| 2021/0170201 A1* | 6/2021 | Berbeco ................ | A61B 90/39 |
| 2023/0051255 A1* | 2/2023 | Yan ...................... | A61N 5/1049 |
| 2023/0204702 A1* | 6/2023 | Miller ................... | G01T 1/10 324/318 |

* cited by examiner

FIXED-POINT MAMMALIAN SPINE-LIKE APPARATUS THAT PROVIDES AN ACCURATE AND FIXED ALIGNMENT POINT OF REFERENCE FOR PRE-TREATMENT CT WHILE PHANTOM AND RADIATION DETECTORS OF A DYNAMIC RADIATION ONCOLOGICAL PHANTOM SYSTEM ARE IN MOTION AND A TUMOR TRACKING BLOCK WITH A TARGET OBJECT OF VARIABLE SIZE, SHAPE, AND DENSITY AND METAL FIDUCIAL MARKERS USED TO MARK TUMORS IN HUMAN TREATMENT

CLAIM OF BENEFIT TO PRIOR APPLICATIONS

This application claims benefit to U.S. Provisional Patent Application 63/459,164, entitled "A FIXED-POINT MAMMALIAN SPINE-LIKE APPARATUS THAT PROVIDES AN ACCURATE AND FIXED ALIGNMENT POINT OF REFERENCE FOR PRETREATMENT CT WHILE PHANTOM AND RADIATION DETECTORS OF A DYNAMIC RADIATION ONCOLOGICAL PHANTOM SYSTEM ARE IN MOTION," filed Apr. 13, 2023. This application also claims benefit to U.S. Provisional Patent Application 63/459,181, entitled "A TUMOR TRACKING BLOCK WITH INNER CHAMBER LIQUID-FORMED EPOXY VOLUME AND METAL FIDUCIAL MARKERS USED TO MARK TUMORS IN HUMAN TREATMENT AND THAT IS CONFIGURED TO FIT INTO A DOCK OF A DYNAMIC RADIATION ONCOLOGICAL PHANTOM SYSTEM AS A TARGET TO TRACK IN COORDINATION WITH A LINEAR ACCELERATOR," filed Apr. 13, 2023. The U.S. Provisional Patent Applications 63/459,164 and 63/459,181 are incorporated herein by reference.

BACKGROUND

Embodiments of the invention described in this specification relate generally to medical dosimetry and radiation oncology quality assurance tools used to simulate tumor motion and patient anatomy during radiotherapy treatments, and more particularly, to (i) a fixed-point mammalian spine-like apparatus to fix alignment in a moving target and (ii) a tumor tracking block with an inner chamber liquid-formed epoxy volume ("target object") of variable size, shape, and density and metal fiducial markers used to mark tumors in human treatment.

A problem in radiation oncology exists because of a mismatch in similarity of a reproducible moving or dynamic patient/phantom device, in which it is not possible to properly represent a patient's case for testing and quality assurance purposes. This is a consequence of the operational nature of the phantom system, which is moving in its whole entirety. However, this does not properly represent an actual patient. For example, the patient's movement may involve respiration, which naturally moves the internal organs, but would not move the patient's spine.

This gives rise to a clear need for a way to fix to a certain point in a moving system, such as a phantom system, so that the alignment point of reference for planning radiologic pre-treatment is proper and accurate, while allowing the phantom with its detectors to be in motion, in order to realistically represent a human patient under treatment.

Furthermore, having a realistic tumor-like target object available to use, or track, is essential when using a dynamic radiation oncological phantom system, such as a Scandidos Delta4 Phantom system with the Hexamotion system, or a SunNuclear ArcCheck with the CIRS motion system, in coordination with a medical Linear Accelerator (hereinafter referred to in short form as "LINAC") such as, preferably, Accuray Radixact or CyberKnife, or any other LINAC.

However, the only existing block for tracking tumor does not provide a realistic representation of a tumor in a human patient since it is made as a simple plastic cube with a perfectly shaped sphere in the exact middle of the block as the target object. This positioning of the target object is so well known that it makes identification and tracking of the target object simple. Additionally, the density of the target object in the sphere of the existing block is notably more dense that the surrounding plastic cube. Once again, this makes the target object easy to be identified and tracked since there is a clear differentiation between the density of the plastic and the density of the target object. In real-world practice, such as with human patients, tumors vary in size, shape, and density with respect to human tissue. The difference—between an exactly positioned, precisely and consistently shaped, and single density target in a model/representation of a tumor and the variability in size, shape, and density of actual tumors in a human patient—is highly consequential when evaluating the ability of the LINAC to track and deliver the radiation treatment plan (such as with the Accuray Synchrony features of the CyberKnife or Radixact LINAC but could apply to any and all LINAC treatments and imaging). For instance, radiation may be inadvertently delivered to health tissue nearby the tumor in the patient if, for example, the shape, size, or density does not conform to the model/representation.

Therefore, in addition to the need for a way to provide a fixed point of reference for proper and accurate alignment in a phantom system for planning radiologic pre-treatment, there is also a need for a tumor tracking item, like a block, a cube, or an elongated 3D rectangle component (or multiple of the same) that can be created to hold one or more target object(s) of variable size, shape, and/or density, and which fits into a dock of a dynamic radiation oncological phantom system as a target to track in coordination with a linear accelerator.

BRIEF DESCRIPTION

A novel fixed-point mammalian spine-like apparatus and a novel tumor tracking block with a variable size, shape, density target object(s) ("target") and metal fiducial markers used to mark tumors in human (or animal) treatment are disclosed. In some embodiments, the tumor tracking block is configured in shape and size to fit into a dock of a dynamic radiation oncological phantom system with the target tracked in coordination with a linear accelerator. In some embodiments, the fixed-point mammalian spine-like apparatus provides an accurate and fixed alignment point of reference for pre-treatment dose delivery evaluation the target is in motion. In some embodiments, the fixed-point mammalian spine-like apparatus includes a connector that attaches to a frame of the phantom system.

In some embodiments, the fixed-point mammalian spine-like apparatus provides an accurate and fixed alignment point of reference for pre-treatment CT (kilo Volt 'kV' or Mega Volt 'MV') while phantom and radiation detectors of a dynamic radiation oncological phantom system are in motion. In some embodiments, the fixed-point mammalian spine-like apparatus comprises (i) a material spine-like structure resembling a mammal spine in shape and density with representations of vertebrae in size, shape, and spacing for a subject patient and (ii) a connector device that attaches the material spine-like structure to a base of a Scandidos Hexmation solid frame (or as a component of the Sun-Nuclear ArcCheck CIRS motion platform) of a dynamic radiation oncological phantom system that is out of an intended CT data view of the volume imaged from treatment preparation. By providing the spine like structure addition to the dynamic phantom's system that is fixed, the alignment point of reference of planning CT data to pre-treatment CT (kV or MV) is proper and accurate, while allowing the phantom with its detectors to be in motion, realistically representing a human under treatment.

In some embodiments, the tumor tracking block is a block made of a plastic material (e.g., a plexiglass-like material) with an inner chamber that is filled with a liquid-formed epoxy volume (target) and metal fiducial markers within the inner chamber liquid that are used to mark tumors in human (or animal) treatment. In some embodiments, the inner chamber of a tumor tracking block varies in shape, size, and/or position to the inner chamber of another tumor tracking block. In some embodiments, the tumor tracking block includes multiple inner chambers with varying sizes, shapes, and density targets at different physical positions within the tumor tracking block. In some embodiments, each inner chamber of the tumor tracking block is formed individually with shape, size, and position variances as needed.

In some embodiments, the target liquid-formed epoxy volume filled in the inner chamber varies in density. In some embodiments, the density of the target liquid-formed epoxy volume is less than the density of the plastic material of the tumor tracking block. In some embodiments, the density of the target liquid-formed epoxy volume is greater than the density of the plastic material of the tumor tracking block.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein.

DETAILED DESCRIPTION

Figure 1:
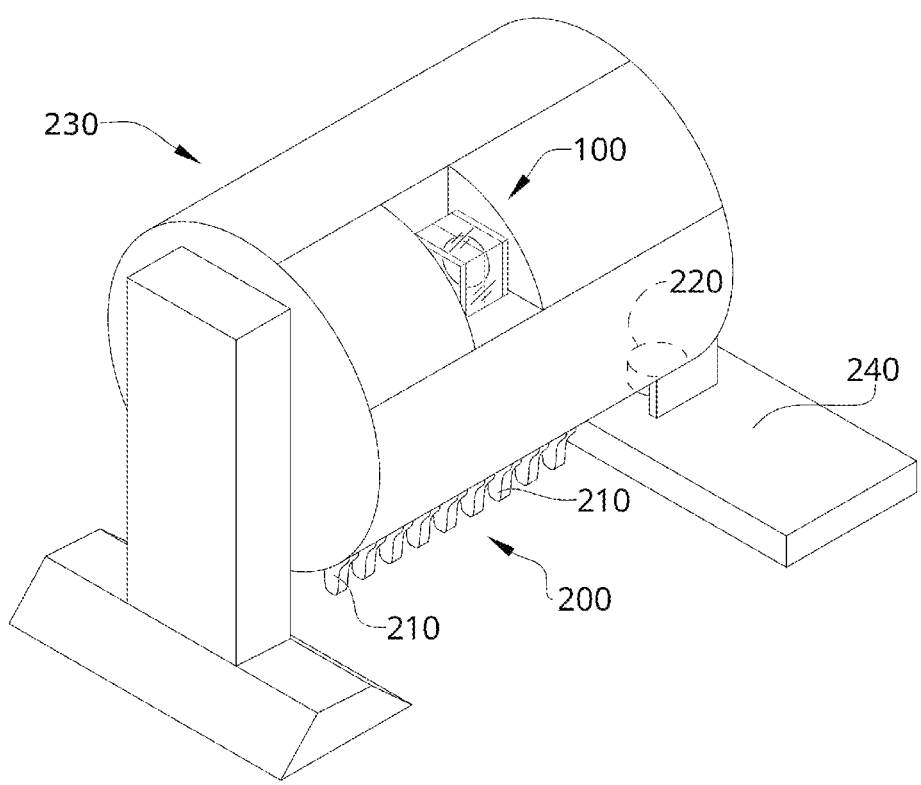
FIG. 1 conceptually illustrates a perspective view of a tumor tracking block and a fixed-point mammalian spine-like apparatus used in connection with a Delta4 phantom system in some embodiments.

In the following detailed description of the invention, numerous details, examples, and embodiments of the invention are described. However, it will be clear and apparent to one skilled in the art that the invention is not limited to the embodiments set forth and that the invention can be adapted for any of several applications. Furthermore, those skilled in the art will recognize that changes in modifications can be made to the exemplary embodiments without departing from the scope of the present disclosure. As used herein, the terms "comprises," "comprising," "includes," "including" and/or any other variation thereof, are intended to cover a non-exclusive inclusion, such that an article (such as a tumor tracking block) and/or apparatus (such as a fixed-point mammalian spine-like apparatus) that comprises a list of elements does not include only those elements but can include other elements not expressly listed and/or inherent to such article, and/or apparatus.

It must also be noted that, as used in this specification and the appended claims, the singular forms "a," "an" and "the" include plural referents unless the content clearly dictates otherwise.

Unless defined otherwise, all technical and scientific terms used herein have the same meaning as commonly understood by one of ordinary skill in the art to which the disclosure pertains. Although a number of apparatuses, tools, machines, methods, and/or materials similar or equivalent to those described herein can be used in the practice of the present disclosure, certain preferred apparatuses, tools, machines, methods, and materials are described herein.

The terms "first," "second," "third," "fourth," and the like in the description and in the claims, if any, are used for distinguishing between similar elements and not necessarily for describing a particular hierarchical, sequential, or chronological order. For instance, in reference to the plurality of plastic blocks, the terms "first rectangle," "second rectangle," "third rectangle," and "fourth rectangle" are used to describe several plastic blocks that form the tumor tracking block and are not necessarily intended to suppose a particular direction, sequence, or order, but are meant to draw attention to their distinct pre-creation quality before the tumor tracking block is formed. Thus, it is to be understood that the terms so used are interchangeable under appropriate circumstances such that the embodiments described herein are, for example, capable of forming the tumor tracking block in other relative forms than those illustrated or otherwise described herein.

The terms "block," "cube," and "3D rectangle component" in the description and in the claims, if any, refer to the same item, namely, the tumor tracking block or the individual plastic blocks that are formed together as the tumor tracking block. Accordingly, when referring to any one of these terms, it is understood to mean that the other terms would apply as would normally occur in practice. For instance, when referring to "the block," it is understood that the term can mean "the cube" or "the 3D rectangle component", and likewise for each such term, and that they refer to "the tumor tracking block".

Furthermore, the terms "comprise," "include," and "have," and any variations thereof, are intended to cover a non-exclusive inclusion, such that an article, an apparatus, an item, a process, a method, a system, or anything else that comprises a list of elements is not necessarily limited to those elements, but may include other elements not expressly listed or inherent to such article, apparatus, item, process, method, or system.

The terms "left," "right," "up," "upward," "down," "downward," "diagonal," and the like in the description and in the claims, if any, are used for descriptive purposes and not necessarily for describing permanent relative positions. For instance, many of the forthcoming descriptions refer to positioning of a target object within a tumor tracking block or relative positioning of multiple target objects within a tumor tracking block. However, it may be understood that the relative positioning descriptions may relate to a particular perspective of viewing the tumor tracking block or that other relative positioning may be possible when the tumor tracking block is created. Therefore, it is to be understood that the terms so used are interchangeable under appropriate circumstances such that the embodiments described herein are, for example, capable of operation in other orientations than those illustrated or otherwise described herein.

Embodiments of the invention described in this specification include both (i) a fixed-point mammalian spine-like apparatus and (ii) a tumor tracking block with a variable size, shape, density target object(s) ("target") and metal fiducial markers used to mark tumors in human (or animal) treatment. In some embodiments, the tumor tracking block is configured in shape and size to fit into a dock of a dynamic radiation oncological phantom system with the target tracked in coordination with a linear accelerator. In some embodiments, the fixed-point mammalian spine-like apparatus provides an accurate and fixed alignment point of reference for pre-treatment dose delivery evaluation the target is in motion. In some embodiments, the fixed-point mammalian spine-like apparatus includes a connector that attaches to a frame of the phantom system.

In some embodiments, the fixed-point mammalian spine-like apparatus provides an accurate and fixed alignment point of reference for pre-treatment CT (kilo Volt 'kV' or Mega Volt 'MV') while phantom and radiation detectors of a dynamic radiation oncological phantom system are in motion. In some embodiments, the fixed-point mammalian spine-like apparatus comprises (i) a material spine-like structure resembling a mammal spine in shape and density with representations of vertebrae in size, shape, and spacing for a subject patient and (ii) the connector (or "connector device") that attaches the material spine-like structure to a base of a Scandidos Hexmation solid frame (or as a component of the SunNuclear ArcCheck CIRS motion platform) of a dynamic radiation oncological phantom system. In some embodiments, the fixed-point mammalian spine-like apparatus attaches to the base of the phantom system frame at a location where it remains out of an intended CT data view of the target volume imaged from treatment preparation. By providing the spine like structure addition to the dynamic phantom's system that is fixed, the alignment point of reference of planning CT data to pre-treatment CT (kV or MV) is proper and accurate, while allowing the phantom with its detectors to be in motion, realistically representing a human under treatment.

In some embodiments, the tumor tracking block is a block made of a plastic material with an inner chamber that is filled with a liquid-formed epoxy volume (target) and metal fiducial markers within the inner chamber liquid that are used to mark tumors in human (or animal) treatment. In some embodiments, the plastic material comprises a polymethylmethacrylate plastic material. In some embodiments, the plastic material comprises one of plexiglass, acrylic, and another polymethylmethacrylate plastic material. In some embodiments, the tumor tracking block comprises a plurality of plastic blocks that are put together to form a block, a cube, a 3D rectangle component, or another shape that is configured to fit within the dock of the dynamic radiation oncological phantom system.

In some embodiments, the plastic material comprises a mixture of plastic epoxy and radioactive material. In some embodiments, the radioactive material is of a liquid state isotope introduced to the epoxy. In some embodiments, the radioactive material (hereinafter also referred to as the "radioactive isotope") is of a liquid state isotope introduced into the inner chamber via a sealable channel that is accessible from an inlet at the surface of the plastic tumor tracking block. In some embodiments, the inlet can be sealed for safety after the radioactive material is introduced into the inner chamber. In some embodiments, the radioactive isotope comprises a mixture of components that are typically used with a positron emission tomography (PET) system and associated PET technology. The PET system and technology may be intended for diagnostic purposes only or the PET system and technology may be compiled to enrich a LINAC system which may focus and track the isotope location within the target object in the phantom system, as would be intended for use in an actual human (or animal) patient, to ensure precise and accurate radiation treatment delivery. The term "epoxy," as used in this specification, is therefore understood to include both radioactive epoxy objects (with radioactive material mixed in) and non-radioactive epoxy objects.

In some embodiments, the inner chamber of a tumor tracking block varies in shape, size, and/or position to the inner chamber of another tumor tracking block. In some embodiments, the tumor tracking block includes multiple inner chambers with varying sizes, shapes, and density targets at different physical positions within the tumor tracking block. In some embodiments, each inner chamber of the tumor tracking block is formed individually with shape, size, and position variances as needed. As such, the tumor tracking block can be made to resemble, as closely as possible, the radiation detecting diode or ion chamber detectors or as far away as the cube available space and as allowed by the dynamic radiation oncological phantom system, whether a Delta4 phantom, an ArcCheck phantom, or another phantom system is used.

In some embodiments, the target liquid-formed epoxy volume filled in the inner chamber varies in density. In some embodiments, the density of the target liquid-formed epoxy volume is less than the density of the plastic material of the tumor tracking block. In some embodiments, the density of the target liquid-formed epoxy volume is greater than the density of the plastic material of the tumor tracking block. In some embodiments, the density of the target liquid-formed epoxy volume is in part less than the density of the plastic material of the tumor tracking block and in other part greater than the density of the plastic material of the tumor tracking block. In some embodiments, the density of the target liquid-formed epoxy volume is the same as the density of the plastic material of the tumor tracking block.

Embodiments of the fixed-point mammalian spine-like apparatus described in this specification solve the problems noted above by providing both a "spine" that is in a fixed location similar to a human patient (or other mammal) with the CT data acquisition and a tumor tracking block with variable size, shape, and density target object and metal fiducial markers. As the lungs and inner organs move with respiration, so moves the dynamic phantom (such as a Delta4 by Scandidos and the Hexamotion system or the ArcCheck by SunNuclear and the CIRS motion platform), but with no fixed structure of reference, the CT acquired data is extremely high in error if taken while moving, or it has to be taken with no motion taking place. This is not advantageous to be represented as the patient-phantom agreement for a radiation plan and for delivery occasions. Similarly, having a target in a block with a fixed location and a known density does not provide accurate evaluation of dosage delivery since actual human tissue and tumors may vary in density, location, size, shape, etc. Thus, providing a spine-like structure that is a fixed, controlled addition to the dynamic phantom system, and using a tumor tracking block with one or more target object(s) of varied size, shape, position, and/or density enables one to evaluate dosage delivery in a way that is in high agreement with respect to a real patient. In a patient, while taking the CT data for radiation planning purposes, or for taking kV or MV CT data in a pre-treatment patient alignment scan, the patient's inner organs, or tumor targets move with respiration takes place, but the actual spine does not move and is a solid reference point to utilize. The fixed-point mammalian spine-like apparatus of the present disclosure provides an improvement to current phantom systems. By using the fixed-point mammalian spine-like apparatus with a phantom system, the overall combined system is improved so that all aspect are as real-time, real-life accurate as possible including, without limitation, the radiation dose actually measured in the dynamic phantom, moving the motion of actual patient respiratory patterns, getting treatment from the medical linear accelerator, and if applicable, the medical linear accelerator's synchrony target tracking system. This provides solid data to confirm that the patient's proposed radiation treatment is safe and providing dose coverage to fulfill the radiation oncologist prescription to the extent intended.

Also, providing a uniquely shaped object with a slightly different density in a plastic cube shaped to exactly fit in the Delta4 phantom or the ArcCheck phantom, tumor tracking for the is vastly improved with respect to true patient outcomes because the target object to track is more realistic to an actual clinical tumor, thereby allowing one to test and evaluate (during pre-treatment) the efficiency of the LINAC's ability to track and deliver the radiation prescription (as provided by a radiation oncologist and delivered by a radiation therapist).

Several more detailed embodiments are described in the sections below. Section I generally describes a fixed-point mammalian spine-like apparatus that provides an accurate and fixed alignment point of reference for pre-treatment dose delivery evaluation when a target is in motion. Section II generally describes a tumor tracking block with a variable size, shape, density target object and metal fiducial markers used to mark tumors in human (or animal) treatment. Section III describes a tumor tracking block and fixed-point mammalian spine-like apparatus used in connection with a Delta4 phantom system. Section III describes a tumor tracking block and fixed-point mammalian spine-like apparatus used in connection with a Delta4 phantom system. Section IV describes formation of a tumor tracking block with different target objects of varying sizes, shapes, positions, and densities and metal fiducial markers used to mark tumors in human (or animal) treatment. Section V describes a tumor tracking block and a fixed-point mammalian spine-like apparatus used in connection with a Delta4 phantom system with a motion platform being utilized to simulate respiration. Section VI describes a tumor tracking block deployed in an ArcCheck phantom system.

I. Fixed-Point Mammalian Spine-Like Apparatus

Embodiments of the fixed-point mammalian spine-like apparatus described in this specification differ from and improve upon currently existing options. For instance, although there is an advantage to a phantom system that is configured to move in a real patient respiratory motion, as opposed to stationary phantoms, the movement of the entire phantom, with its radiation measuring diodes or chambers has a problem as there is no fixed point from which to take pre-treatment alignment measurement points, while the phantom motion system is engaged, leaving the medical linear accelerator system (such as Accuray's Synchrony system) lacking in similarity to the actual human (whose pre-treatment alignment actually has with their stationary spine structure). In other words, there are either radiation phantoms that are totally stationary, or phantoms that are dynamic, but there are none that have both a fixed structure-point and moving radiation detectors (be that ion chambers or diodes) trying to best represent a patient. This prevents true realistic investigation of the dose measured from the patient's treatment and its actual planned intention.

However, there is nothing like the improved provided by the fixed-point mammalian spine-like apparatus available in the world yet. Specifically, the fixed-point mammalian spine-like apparatus provides a fixed structure-point and moving radiation detectors (be that ion chambers or diodes) trying to best represent a patient under treatment.

The fixed-point mammalian spine-like apparatus of the present disclosure may be comprised of the following elements. This list of possible constituent elements is intended to be exemplary only and it is not intended that this list be used to limit the fixed-point mammalian spine-like apparatus of the present application to just these elements. Persons having ordinary skill in the art relevant to the present disclosure may understand there to be equivalent elements that may be substituted within the present disclosure without changing the essential function or operation of the fixed-point mammalian spine-like apparatus.

1. A mammal spine's physical density is similar to material formed or shaped in a spine like structure to best represent the vertebrae in size, shape, and spacing.
2. A device ("connector") that attaches the spine structure to the base of the Hexmation solid frame that is out of the intended CT data view of the volume imaged from treatment preparation.

The various elements of the fixed-point mammalian spine-like apparatus of the present disclosure may be related in the following exemplary fashion. It is not intended to limit the scope or nature of the relationships between the various elements and the following examples are presented as illustrative examples only. The spine-like structure is ideally of similar density to mammal bone however it can be any density that can be used for CT planning purposes or CT alignment purposes. Therefore, the density can be of a range, not specific electron density or atomic structure density. The spine structure is best intended to be as similar to a spine shaped structure in shape, material, and density, but can be any fixed object that has any shape, any size, or having any distinguishable points that can be used to make planned CT image to pre-treatment alignment CT image (kV or MV), or planned CT data to pre-treatment alignment any modality image (such as kV x-ray or MR imaging, or PET image technology). As for the attaching component (connector), it can be a fixed device that holds the spine-like structure in a solid position to a frame of the phantom system. The connector can also be a device that allows the spine-like structure to be moved to a different position in relation to a previous position, be that an angle on the X-Y, or X-Z, or Z-Y plane, or rotation about any of the coordinate axis such it be different that the simple fixed location. The connector can have a rotation measure reference marking system to control and replicate certain angles moved. The spine-like structure is, as mentioned, best representing when it looks like a mammalian spine, but it can be any fixed structure that may be more than a single structure, such as two of three structures that can be used as reference.

The fixed-point mammalian spine-like apparatus of the present disclosure generally works in the following manner. When the planning reference of the phantom system is taken, install the spine structure to the fixed frame of the movement device (i.e., the Scandidos Hexamotion solid frame of the Delta4 by Scandidos). As it is placed in its designed location, this will allow the spine structure (hereinafter also referenced simply as the "spine") to be positioned in a layout at the physicist, or physician, or dosimetrist, or therapist, or whoever is preparing the phantom system for the CT image controlled intended, desirable position. This position of the spine can be noted if different than a fixed-no-angle layout modification to assure replication on the treatment table as was positioned on the image CT table. The phantom can be set into motion replicating the real life patient's respiratory pattern (whichever type of breathing chosen is irrelevant to the situation due to the spine being used as the intended point of planning CT to pre-treatment alignment). Take the planning imaging CT data of the phantom system, the phantoms in or not in motion at the controller's desire, including the spine which will be a relative location to a real person (e.g., on the table surface in a relative real person's spine location as the person's torso region would be imaged). Transfer to the planning system. Create a phantom system reference to be at use to create a patient phantom quality assurance (QA) plan. When a patient has their image data taken of the moving tumor target (e.g., a tumor in the lung or on the liver, diaphragm, kidney, etc.), create the treatment plan. When that is complete, create the QA plan using the phantom CT data taken with the spine. Place the patient's treatment data onto the phantom treatment data in a manner that includes the spine structure. Make the plan and have the planning software compute the intended dose delivery to the phantom that will be used as reference to the dose that is actually delivered when the QA plan is performed. The Scandidos Delta4 phantom system (D4) is referred to below as "Hexamotion and Accuray Radixact" with synchrony feature, but can any LINAC or dynamic phantom (such as SunNuclear's CIRS motion platform or any other motion platform and, for that matter, any LINAC, such as a LIANC model from Varian or Elekta or any other LINAC system, be that of X-ray, gamma ray, neutron, or proton treatment plan delivery) that may come into existence. Place the D4 on the treatment table. Set the D4 into motion. align the system with the lasers to a predesignated point on the stationary spine. Perform the alignment scan. Ignore the image of the moving phantom or targets within. Align the pre-treatment image to the planning image reference to the spine point. After adjustment to best fit the planning image spine to pre-treatment spine is complete, begin the delivery of the QA plan, with the phantom in motion similar to a real lung, or any in-motion organ target. When complete, perform the analysis of dose data planned vs delivered and evaluate conclusion. By using a moving data collected phantom that moves like a real person, making the tumor target move as well, while referencing treatment delivery position to the spine, as would be done to a real patient (for example a Radixact Synchrony lung patient), the actual effectiveness and safety of the treatment plan be judged. This will show what tissue intended to be treated and spared from radiation is actually treated and spared in the most real life patient motion situation giving the most true values.

To make the fixed-point mammalian spine-like apparatus of the present disclosure, the spine can be made by shaping any material such as plastic rods, or fiberglass rods, or wooden rods, etc. where it can be shaped by sanding or cutting as needed to best look like and be a replicate of an actual human spine (or just be a fixed non-moving substitute object with same intent in mind). If a real mammal spine is to be used, provided it is done legally and placed in an epoxy that will encompass the spine such it will be in a controlled and sterilized form, that would be sufficient. It could also be made by piecing each vertebrae together by a rope like flexible or solid rod to obtain a planned and controlled layout. This spine will then be attached to the linking device that will hold it in place to the frame of the motion system of the phantom system such it is of a controlled position. It can be held in place to the spine by epoxy or metal screws etc., or plastic devices to avoid a potential metal artifact in the CT image. This will then be attached to the motion system from by a secure fastening, bolts and nuts appropriate. The linking device can also have a rotating composition that could allow the modification of the angle of the spine in reference to the sagittal plan, or coronal plane.

To use the fixed-point mammalian spine-like apparatus of the present disclosure, it is used as a fixed reference point in a dynamic phantom system that is replicating a real patient's spine and dynamic torso such will be ideal for investigation of treatment plans using the Accuray Radixact or CyberKnife Synchrony system, or any treatment delivery system, but also provide illumination to the actual dose delivered by any treatment of any linear accelerator of a patients plan via delivery to the dynamic phantom system.

II. Tumor Tracking Block

Embodiments of the tumor tracking block with inner chamber liquid-formed epoxy volume and metal fiducial markers described in this specification differ from and improve upon currently existing options. Specifically, the only current block to be used in a phantom system also has the disadvantage of being perfectly in the middle of the cube. This fact rises more margin of error as it is further away from the diode detecting boards. Due to the fact that radiation is an inverse law phenomenon, slight differences that need not be present significantly amplify the error of exposure or the ability to measure with precision. However, the tumor tracking block with inner chamber liquid and metal fiducial markers of the present disclosure provides density that is very similar to the plastic that surrounds it, as well as the 3D shape of the tumor target object is not a symmetric unnatural shape taken by tumors. It is a unique non-symmetrical shape that is synonymous with an actual tumor (which is the mission or purpose that the block is supposed to serve). By providing density at block creation time, it is possible to shape the target objects in the cube to be any size and or shape (from very very small to very very large up to the entire volume of the block), as well as the location of the tumor tracking object in the block. This results in making a tumor tracking block that closely resembles the intended subject of the radiation treatment placed in the block in location to the radiation detecting diodes or ion chamber detectors as close to or as far away as the cube available space in the Delta4 phantom, or ArcCheck or any other (unnamed) phantom system as allowed.

The tumor tracking block with inner chamber liquid-formed epoxy volume and metal fiducial markers of the present disclosure may be comprised of the following elements. This list of possible constituent elements is intended to be exemplary only and it is not intended that this list be used to limit the tumor tracking block with inner chamber liquid and metal fiducial markers of the present application to just these elements. Persons having ordinary skill in the art relevant to the present disclosure may understand there to be equivalent elements that may be substituted within the present disclosure without changing the essential function or operation of the tumor tracking block with inner chamber liquid and metal fiducial markers.

1. Plexiglass style plastic, or another style of polymethylmethacrylate plastic, such as acrylic, with a certain known density (in a preferred embodiment, plexiglass with a density of roughly 1.2 g/cm$^3$, which is similar to water, roughly 1.0 g/cm$^3$, or as close to water as possible ideally). This plexiglass plastic is the material that is used to compose the cube for the tumor tracking block and is needed to fit into the dock in the Scandidos Delta4 Phantom System, or, alternately, used to compose a slide block component (or components) to fit in the inner volume of the SunNuclear ArcCheck Phantom system.
2. An epoxy style liquid that can be of a density less than water to a density greater than water.
3. Metal fiducial markers. This can be simple metal commonly used in medical practice for markers or rare earth metals such as gold fiducial markers that are best used to mark tumors in human treatments.

The various elements of the tumor tracking block with inner chamber liquid-formed epoxy volume and metal fiducial markers of the present disclosure may be related in the following exemplary fashion. It is not intended to limit the scope or nature of the relationships between the various elements and the following examples are presented as illustrative examples only. The plastic cube can be the size that exactly fits in the slotted area designated or it could be slightly less. Just as long as the cube fits, it is a functional object. The epoxy to be used can be many densities and colors. It could be a solid piece used to insert in the block as well, predesigned and created such to fit in the cube anywhere. The space that the tracking object will fit in can be many sizes and shapes and in any location in the block. The fiducial markers can be placed also in any location in the block, possibly outside and inside, the tracking target object. There can be as few markers as none to as many as desired. They can be fiducial markers of shapes, sizes and composition of whatever material wanted. Just as long as they are fiducial markers inserted such like would be in a real life mammal cancer tumor treatment case.

The tumor tracking block with inner chamber liquid and metal fiducial markers of the present disclosure generally works by cutting the plexiglass into components (one to many) which, when combined with any kind of adhesive substance, will form the cube of desired size. The pieces, before being put together, will have unique or abnormal shaped volumes carved out, using any tool found appropriate for doing this function. This void will be filled with the epoxy substance (or the pre-designed object that will be placed in to serve the same purpose as a tracking object able to be seen in the CT image). The location of the epoxy deposit or object can be made anywhere in the cube or any size, but best located in or towards one of the corners of the cube such that this location will be closest to the most dense, closest shaped detectors of the Delta4, yielding the most accurate measurements. The cube components also can have the metal fiducial markers placed in any location, but best located in arrangements that are not co-planar to best represent what would be desirable in a human case.

To make the tumor tracking block with inner chamber liquid and metal fiducial markers of the present disclosure, start by cutting the plexiglass into components (one to many or "1 M") which, when combined with any kind of adhesive substance, will form the cube of desired size. For instance, you may cut two pieces of the plexiglass plastic material in the dimensions of the needed space to be filled in the Delta4 or the ArcCheck. The pieces, before being put together, will have unique or abnormal shaped volumes carved out, using any tool found appropriate for doing this function. For example, a person could just use a drill or machining tool to carve a void from the plastic that is unique and not symmetrical (although it could be if wanted) in a manner that it will represent half of the final total object (or whatever fraction of the object each plastic component represents). This void will be filled with the epoxy substance (or the pre-designed object that will be placed in to serve the same purpose as a tracking object able to be seen in the CT image). The epoxy substance would be the inner chamber liquid (in whatever density) and would solidify to form the solid that will fill the created void (or the solid object already made). Yet, the location of the epoxy deposit can be made anywhere in the cube or for any size, but would be best located in or towards one of the corners of the cube such that this location will be closest to the most dense, closest shaped detectors of the Delta4, or at a location in the ArcCheck that would be furthest or closest to the detectors as of how they are laid out in the ArcCheck phantom, yielding the most accurate measurements. The solid epoxy would need to agree with the plastic surface, and when confirmed, the person could just glue or combine the plastic pieces together in way that the epoxy object parts will unite and form a shared volume making them a 3D shaped object in the block.

The cube components also can have the metal fiducial markers placed in any location, but best located in arrangements that are not co-planar to best represent what would be desirable in a human (or any animal) case (what this is modeling after and representing). To add the markers, the person could have also inserted them into the plastic pieces (before putting them together to form the cube) in locations that are most suitable for the tracking object that best represents what would occur in a real case with a real human patient case.

In some embodiments, the epoxy substance and/or the fiducial markers may be left out. In other words, there could be a cube with just fiducial markers and a cube with just the epoxy object in it, or there can be a cube with both epoxy and fiducial markers combined. In some other embodiments, the inner chamber is entirely filled with a liquid isotope. In some embodiments, the liquid isotope that is used to entirely fill the inner chamber comprises a radioactive tracing material ("radioactive tracer"). In some embodiments, the radioactive tracer comprises Fluorodeoxyglucose (also known, and hereinafter referred to, as "FDG"). In some embodiments, the liquid isotope that is used to entirely fill the inner chamber comprises any other radioactive tracer. In some embodiments, the fiducial markers are radioactive. In some embodiments, the radioactive material of the fiducial markers comprises short half-life radioactive isotopes. In some embodiments, the radioactive material of the fiducial markers comprises long half-life radioactive isotopes. In some embodiments, the epoxy-filled inner chamber includes one or more radioactive isotope source(s).

In some embodiments, there are multiple objects in the cube. These (presumably) epoxy objects can be near each other or away from each other and can have a common (same) density or different densities. By having multiple objects in the cube, one would be able to test the ability to discern one object form the other in the tracking and radiation dose delivering treatment. There can be just the unfilled void in cube as well to represent air or anything desired to fill the void. The cube can be put in the Delta4 or ArcCheck in any angle or coordinate chosen. This will make the tracking target be at other locations in the phantom(s) further testing the ability of tracking and delivering the radiation dose.

To use the tumor tracking block with inner chamber liquid-formed epoxy volume and metal fiducial markers of the present disclosure, a person would place the cube in the Delta4 or ArcCheck (or any applicable phantom) and perform a CT scan (or any desired planning scan modality as seen as appropriate) of the system to be used for radiation treatment planning. The person may create the plan and place the Delta4 or ArcCheck (or any applicable phantom) on the LINAC treatment table in with the cube in the same coordinate system as it was when the CT image was taken for planning. Then the person could coordinate or configure the LINAC (or here on Accuray Radixact be used for example) to use the object in the cube in the Delta4 or ArcCheck (or any applicable phantom) as the tracking object. The person could set the Delta4 in motion with the Hexamotion movement system or the ArcCheck in motion with the CIRS motion system that it is associated and have the Radixact track and deliver the dose the to the tracking object. The person may evaluate the dose delivery to the planned dose delivery. Then decide if this plan is acceptable to be delivered to the patient of which this treatment process this was representing as the Quality Assurance test.

III. Tumor Tracking Block and Fixed-Point Mammalian Spine-Like Apparatus Used in Connection With a Delta4 Phantom System By way of example, FIG. 1 conceptually illustrates a perspective view of a tumor tracking block and a fixed-point mammalian spine-like apparatus used in connection with a phantom system. Specifically, a tumor tracking block 100 is placed in a phantom system 230 with a fixed-point mammalian spine-like apparatus 200 attached to a frame 240 of the phantom system 230 by a connection device 220. In particular, the fixed-point mammalian spine-like apparatus 200 includes several vertebrae 210 spaced similar to a human subject (or other mammalian subject). Also, this figure demonstrates placement of the tumor tracking block 100 in, and attachment of the fixed-point mammalian spine-like apparatus 200 to, a Scandidos Delta4 phantom system 230.

Figure 2:
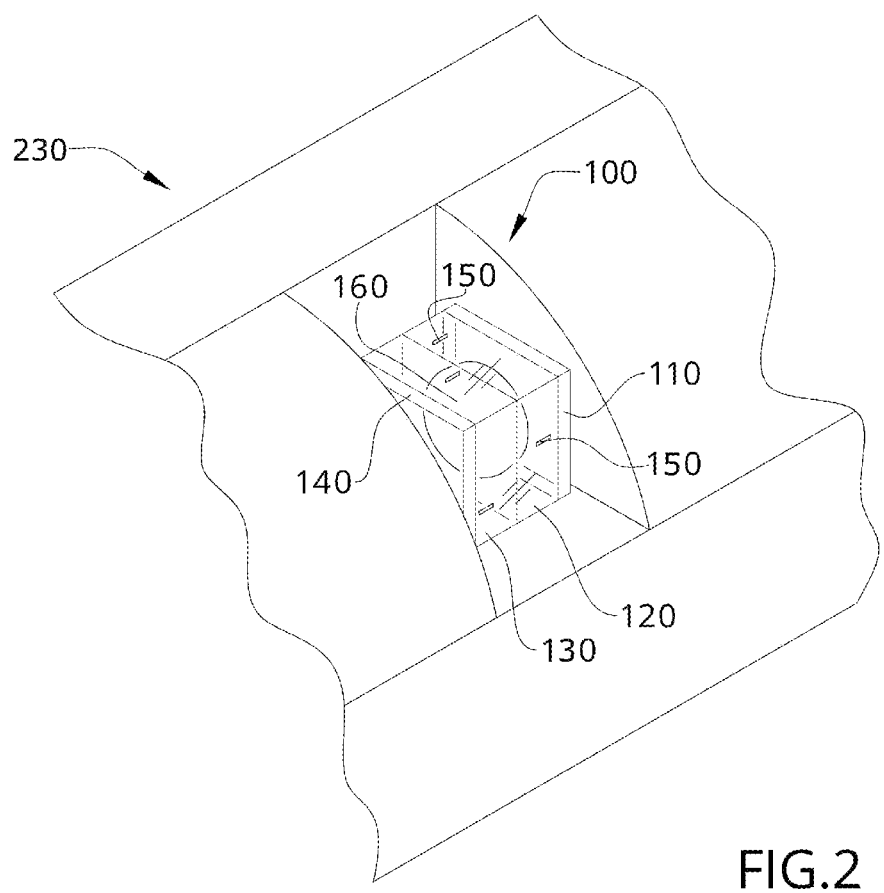
FIG. 2 conceptually illustrates a detailed perspective view of the tumor tracking block placed in the Delta4 phantom system in some embodiments.
Figure 3:
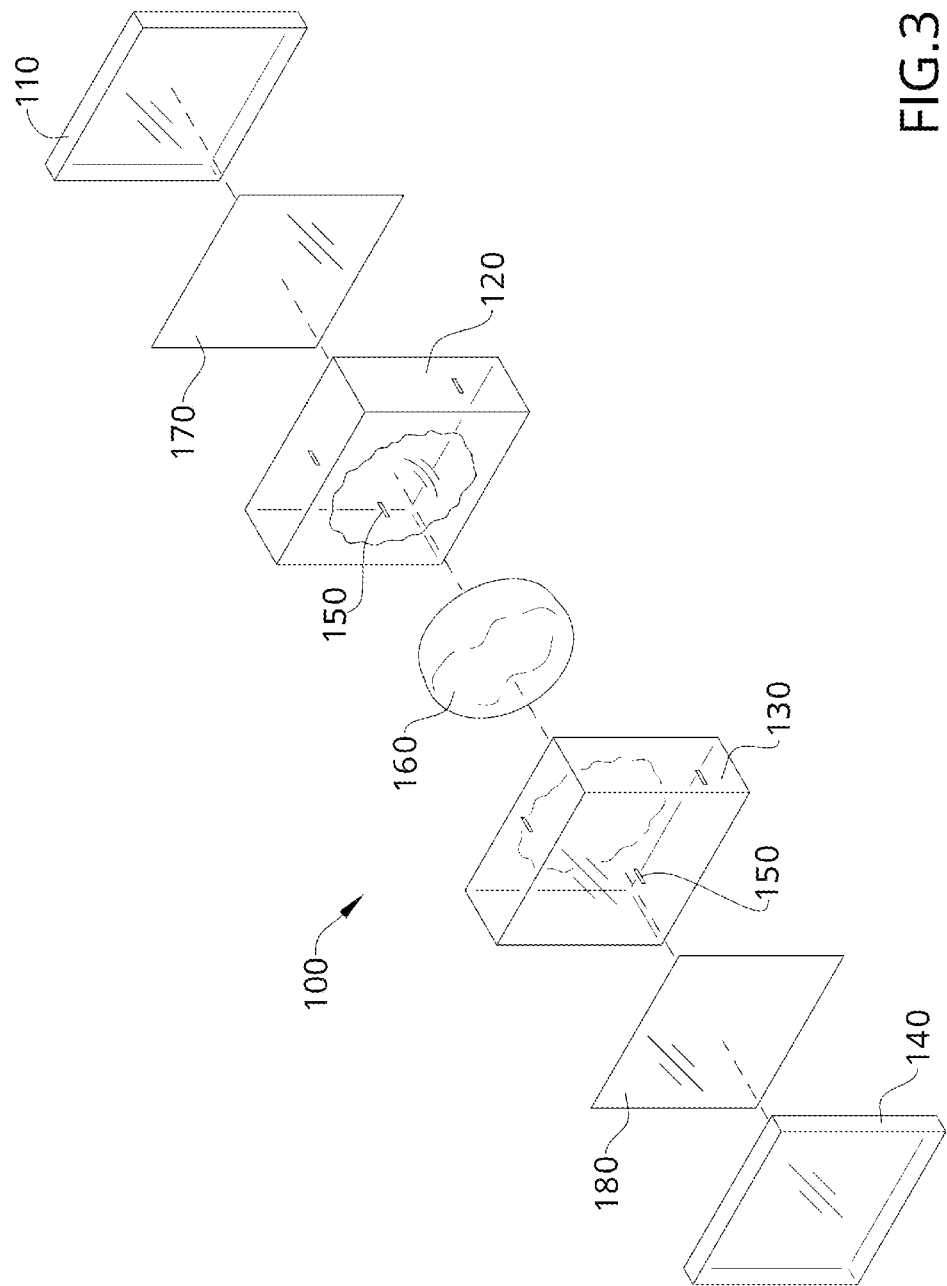
FIG. 3 conceptually illustrates an exploded view of a tumor tracking block with a target object and metal fiducial markers used to mark tumors in human (or animal) treatment.
Figure 4:
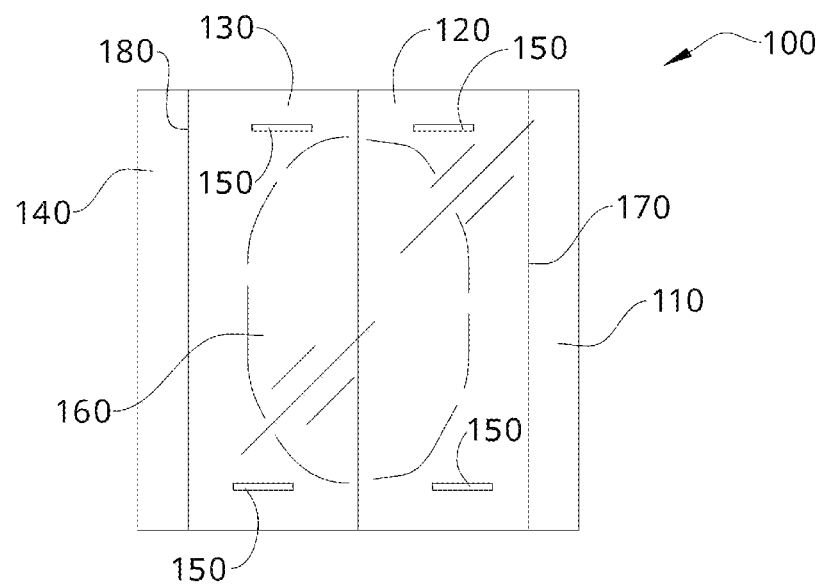
FIG. 4 conceptually illustrates a side view of the tumor tracking block fully-formed with the single target object and metal fiducial markers in some embodiments.

Now turning to another view, FIG. 2 conceptually illustrates a detailed perspective view of the placement of the tumor tracking block 100 in the phantom system 230. Also, the tumor tracking block 100 shown in this detailed view demonstrates several components the make up the tumor tracking block 100 including a first rectangle 110, a second rectangle 120, a third rectangle 130, a fourth rectangle 140, a plurality of metal fiducial markers 150, and a target object 160. Together, the first rectangle 110, the second rectangle 120, the third rectangle 130, and the fourth rectangle 140 form the structure of the overall tumor tracking block 100 in which the target object 160 and fiducial markers 150 are encapsulated. Details of tumor tracking block 100 creation and formation are described in the next section, by reference to FIGS. 3-6.

IV. Formation of a Single Target Tumor Tracking Block and a Multi-Target Tumor Tracking Block With Different Target Objects of Varying Sizes, Shapes, Positions, and Densities and Metal Fiducial Markers By way of example, FIG. 3 conceptually illustrates an exploded view of the tumor tracking block 100 with a target object and metal fiducial markers used to mark tumors in human (or animal) treatment. Specifically, the tumor tracking block 100 shown in this figure includes the first rectangle 110, the second rectangle 120, the third rectangle 130, the fourth rectangle 140, the plurality of fiducial markers 150, the target object 160, a first film insert 170, and a second film insert 180. An inner chamber is carved out the second rectangle 120 and the third rectangle 130 so that when they are joined together, the target object 160 is filled inside the chamber. Fiducial markers 150 are also shown at various locations throughout the second rectangle 120 and the third rectangle 130. The tumor tracking block 100 is created by joining all the components together. In this exemplary tumor tracking block 100, the first film insert 170 is positioned at a junction between the first rectangle 110 and the second rectangle 120 while the second film insert 180 is positioned at the junction between the third rectangle 130 and the fourth rectangle 140. As mentioned, the target object 160 fills the inner chamber carved out of both the second rectangle 120 and the third rectangle 130.

After the tumor tracking block 100 is created, it forms a full block ready for placement in the phantom system. A fully-formed tumor tracking block 100 is described next, by reference to FIG. 4. Specifically, FIG. 4 conceptually illustrates a side view of the tumor tracking block 100 fully-formed with the target object 160 and the plurality of metal fiducial markers 150. As can be seen, the first film insert 170 fits in the junction between the first rectangle 110 and the second rectangle 120. Similarly, the second film insert 180 fits in the junction between the third rectangle 130 and the fourth rectangle 140. The plurality of fiducial markers 150 are positioned at various locations within the second rectangle 120 and the third rectangle 130, with the target object 160 spreading out over the junction between the second rectangle 120 and the third rectangle 130. Note, the fiducial markers 150 in some embodiments are positioned at locations with the target object 160, but not shown in this figure so as not to obscure other aspects shown in this view. Also note that the tumor tracking block 100 can be created to contain multiple target objects of different sizes, shapes, positions, and/or densities. An example of multiple targets in a single tumor tracking block is described next, by reference to FIGS. 5 and 6.

Figure 5:
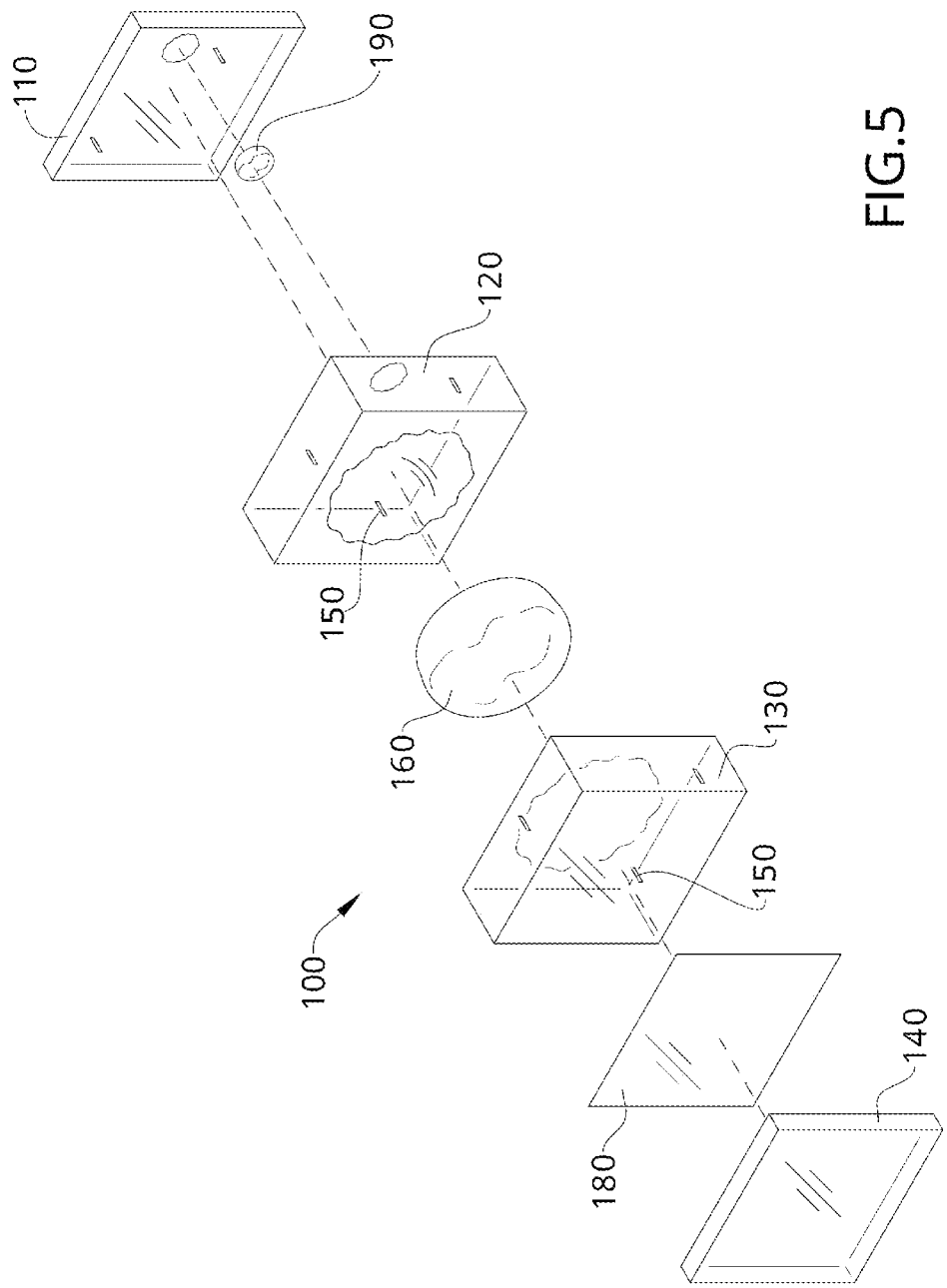
FIG. 5 conceptually illustrates an exploded view of a tumor tracking block with multiple, different target objects of varying sizes, shapes, positions, and densities and metal fiducial markers used to mark tumors in human (or animal) treatment.

In particular, FIG. 5 conceptually illustrates an exploded view of a tumor tracking block 100 with the fiducial markers 150 and multiple, different target objects of varying sizes, shapes, and positions (as can be seen), as well as having different densities. In this figure, the first film insert 170 is removed for clarity in showing a second target object 190 that is smaller than the original target object 160. This second target object 190 is positioned within the tumor tracking block 100 at a different location than the target object 160. The second target object 190 is also smaller in size than the original target object 160 and, therefore, fills a smaller inner chamber (at the different position and with a different shape) carved out of the first rectangle 110 and the second rectangle 120, with fiducial markers in both the first rectangle 110 and the second rectangle 120.

Figure 6:
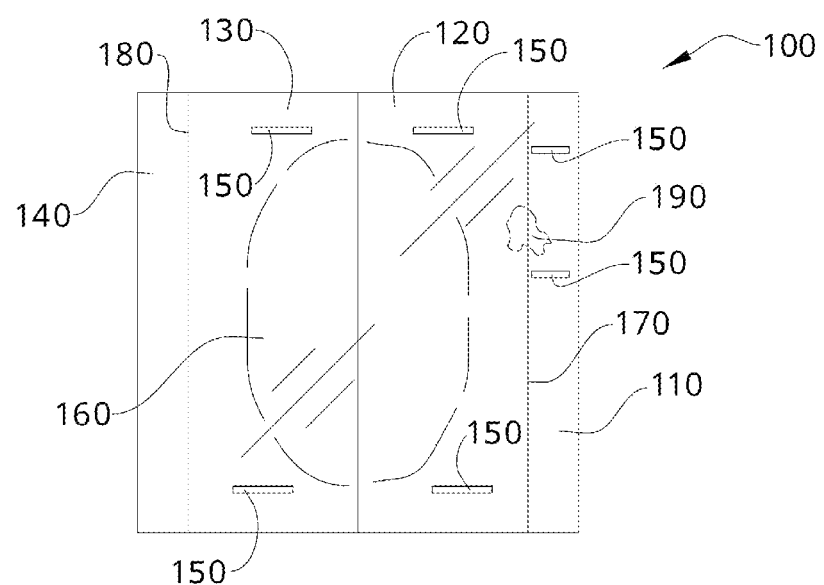
FIG. 6 conceptually illustrates a side view of the tumor tracking block fully-formed with multiple, different target objects of varying sizes, shapes, positions, and densities and metal fiducial markers in some embodiments.

In a more detailed view of the tumor tracking block with multiple targets, and by way of reference, FIG. 6 conceptually illustrates a side view of the tumor tracking block 100 fully-formed with multiple, different target objects of varying sizes, shapes, positions, and densities and with fiducial markers 150 used to mark tumors in human (or animal) treatment. As shown in this figure, the second target object 190 spans the junction between the first rectangle 110 and the second rectangle 120. Along with the original target object 160, the second target object 190 provides a more life-like evaluation for the system, since human tumors sometimes arise in multiple, different locations, with different shapes and/or sizes. Furthermore, the second target object 190 may be filled with a more dense or less dense liquid-formed epoxy, as compared to that of the original target object 160, to simulate different tumor densities.

Figure 7:
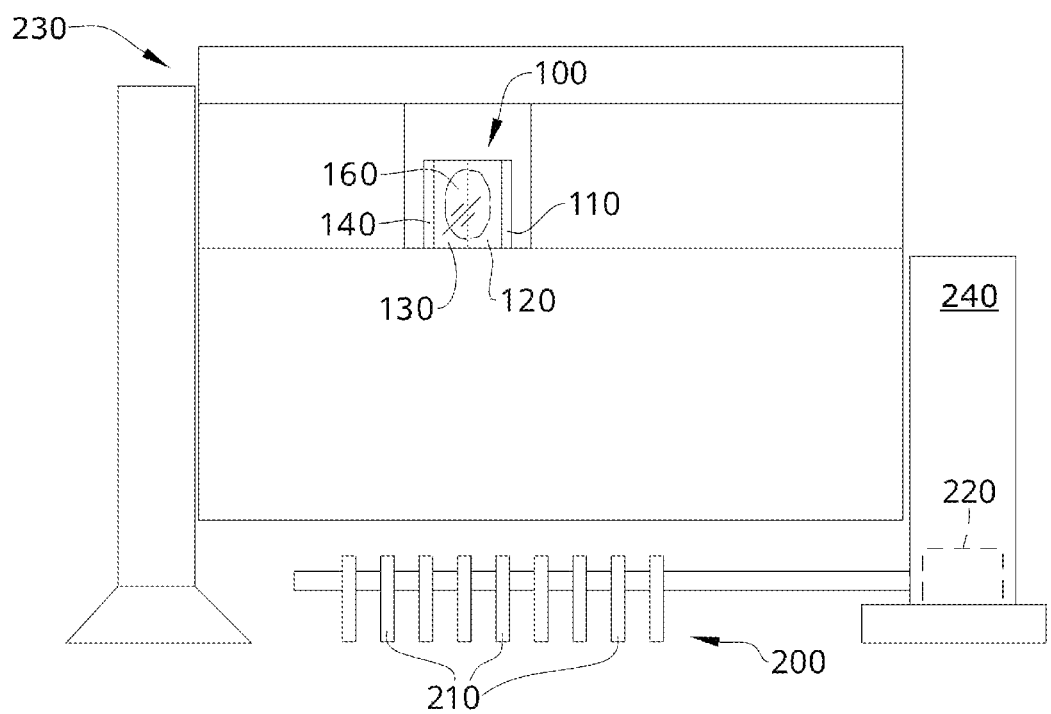
FIG. 7 conceptually illustrates a side view of the Delta4 phantom system with a connection device that attaches the fixed-point mammalian spine-like apparatus to a frame of the Delta4 phantom system in some embodiments.

V. Tumor Tracking Block and Fixed-Point Mammalian Spine-Like Apparatus Used in Connection With a Delta4 Phantom System With a Motion Platform Being Utilized to Simulate Respiration By way of example, FIG. 7 conceptually illustrates a side view of the fixed-point mammalian spine-like apparatus 200 attached to the connection device 220, which itself is attached to the frame 240 of the phantom system 230. In this figure, the phantom system 230 demonstrates relative placement of the fixed-point mammalian spine-like apparatus 200 when attached, via connection device 220, to a Scandidos Delta4 phantom 230. Also, this figure provides a more accurate visual representation of spacing between the individual vertebrae 210 of the fixed-point mammalian spine-like apparatus 200. Furthermore, the tumor tracking block 100 is clearly shown inserted into the Delta4 phantom 230, which allows for evaluation of the treatment (by the LINAC) to the target object 160 in the tumor tracking block 100 while the Delta4 phantom 230 simulates motion (e.g., simulating a human subject breathing during treatment). In the case of the Delta4 phantom system 230, the motion platform utilized may be the Hexamotion system by Scandidos. This is described next, by reference to FIG. 8.

Figure 8:
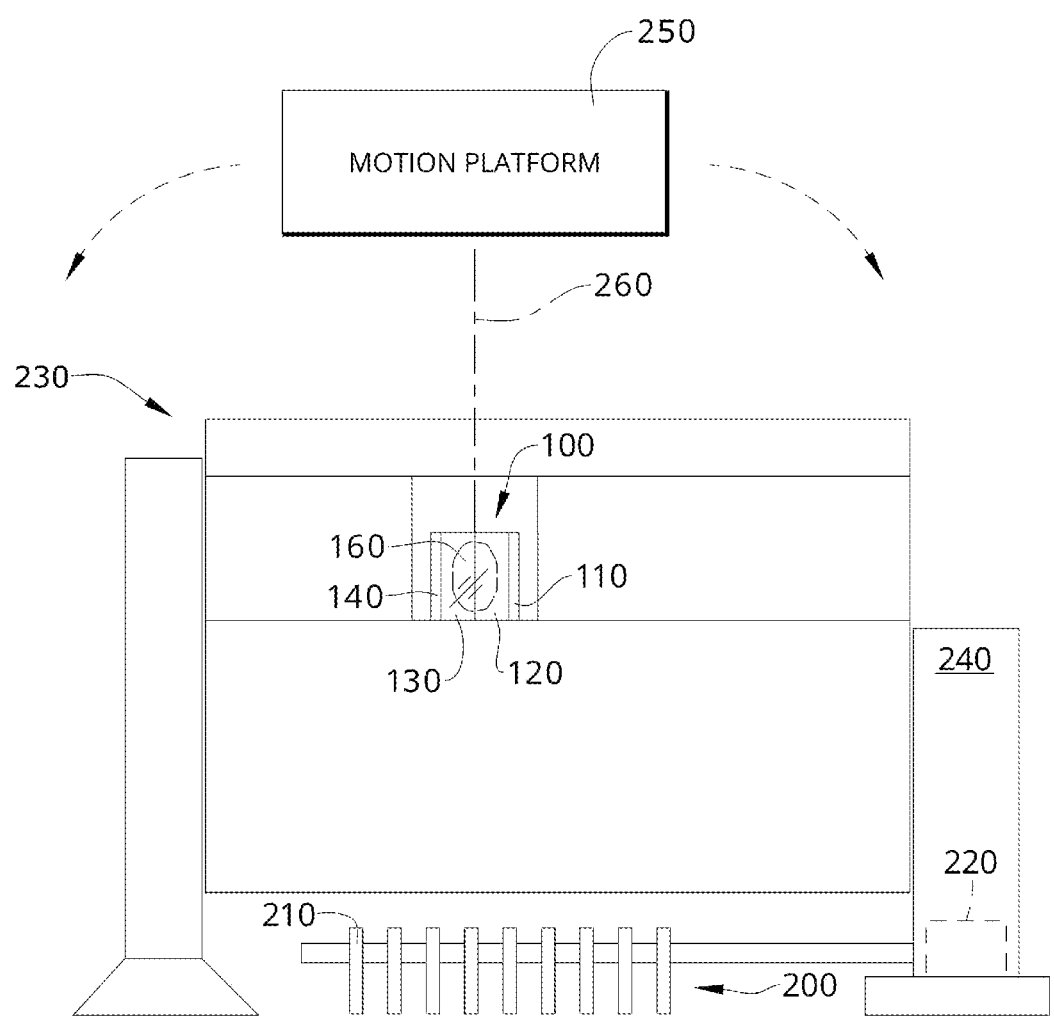
FIG. 8 conceptually illustrates a side view of a motion platform being utilized by the phantom system to simulate respiration with the tumor tracking block placed for dosage delivery evaluation and the fixed-point mammalian spine-like apparatus attached for fixed alignment in some embodiments.

Specifically, FIG. 8 conceptually illustrates a side view of a motion platform (e.g., the Hexamotion system by Scandidos) utilized by the phantom system (e.g., the Delta4 phantom system by Scandidos) to simulate respiration with the tumor tracking block placed for dosage delivery evaluation and the fixed-point mammalian spine-like apparatus attached for fixed alignment in some embodiments. As shown in this figure, the tumor tracking block 100 includes the target object 160 encapsulated within the block, after full formation of the first rectangle 110, the second rectangle 120, the third rectangle 130, and the fourth rectangle 140 (as well as with fiducial markers and film inserts, neither of which are shown in this figure). The tumor tracking block 100 is placed in the phantom 230 (in this case, the Delta4 phantom 230) at a position in which the LINAC is able to deliver the treatment dosage via scanning beam 260. When the phantom system 230 is in motion (to simulate respiration), the fixed-point mammalian spine-like apparatus 200 remains in fixed location (as a human subject's spine would not move while the lungs of the patient inhale and exhales, resulting in motion only in and around the upper torso area of the subject). The motion platform 250 continues to simulate the motion while the LINAC delivers treatment while this is tracked to determine whether the dosage is delivered exclusively to the tumorous target 160 or imprecisely delivered to both the target 160 and surrounding (healthy) tissue. Similarly, if the tumor tracking block 100 had encapsulated two or more target objects (such as different targets with different sizes, shapes, positions, and/or densities), the motion would be simulated by the motion platform 250 for the phantom system 230 while the LINAC delivers the treatment 260 to, ideally, both (or all of) the targets. In this way, by using the tumor tracking block 100 with one or more realistic target objects at various positions, sizes, shapes, and/or densities, one can easily track the dosage delivery to determine whether the treatment plan can be accurately carried out by the LINAC.

While the information described above, by reference to FIGS. 1-2 and 7-8, relate to applications of a Delta4 phantom system and Hexamotion system as a motion platform, the tumor tracking block and the fixed-point mammalian spine-like apparatus of the present disclosure can also be applied to other types of phantom systems. In the next section, a different type of phantom system is utilized—specifically, an ArcCheck phantom system by SunNuclear with the CIRS motion system.

VI. Tumor Tracking Block Utilized in an ArcCheck Phantom System

Figure 9:
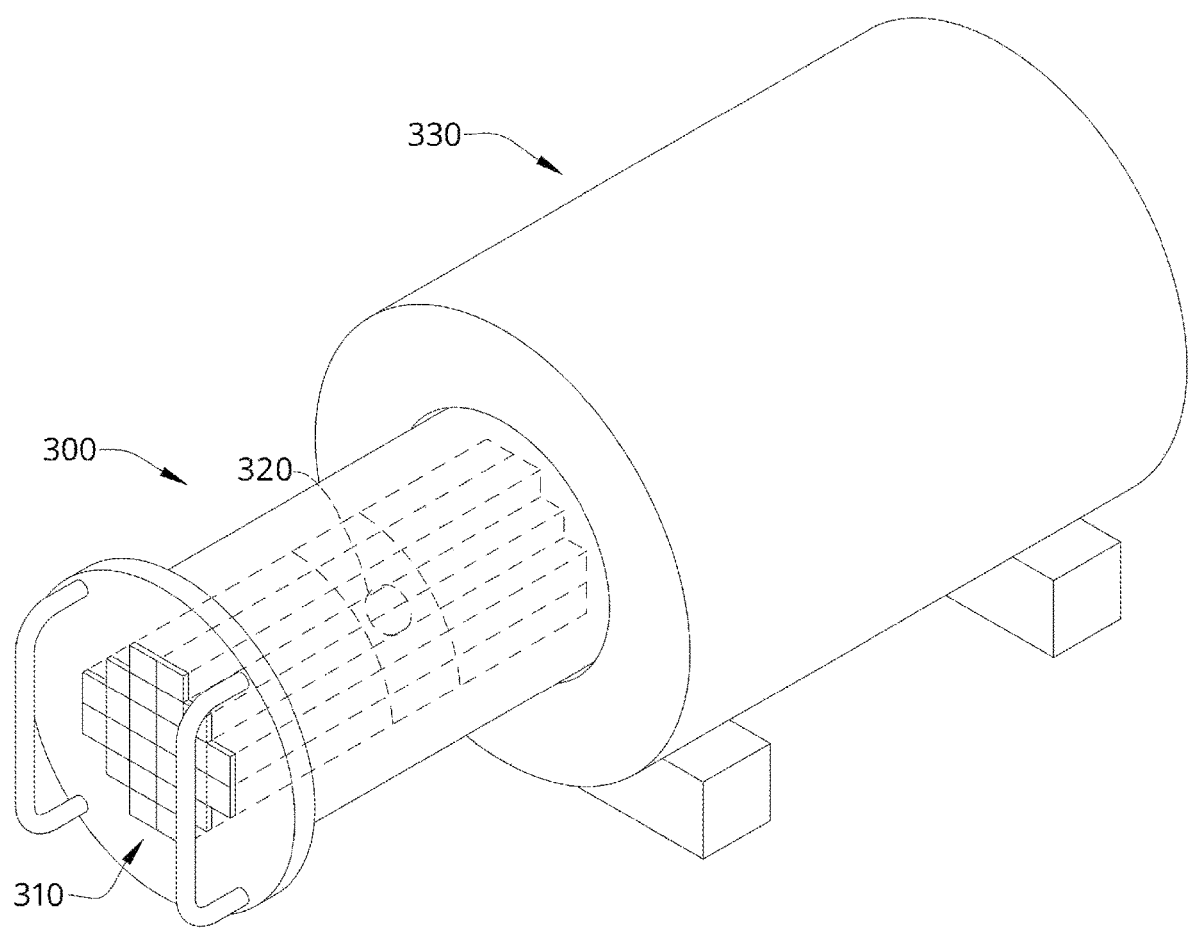
FIG. 9 conceptually illustrates a perspective view of a tumor tracking block placed in an ArcCheck phantom system in some embodiments.
Figure 10:
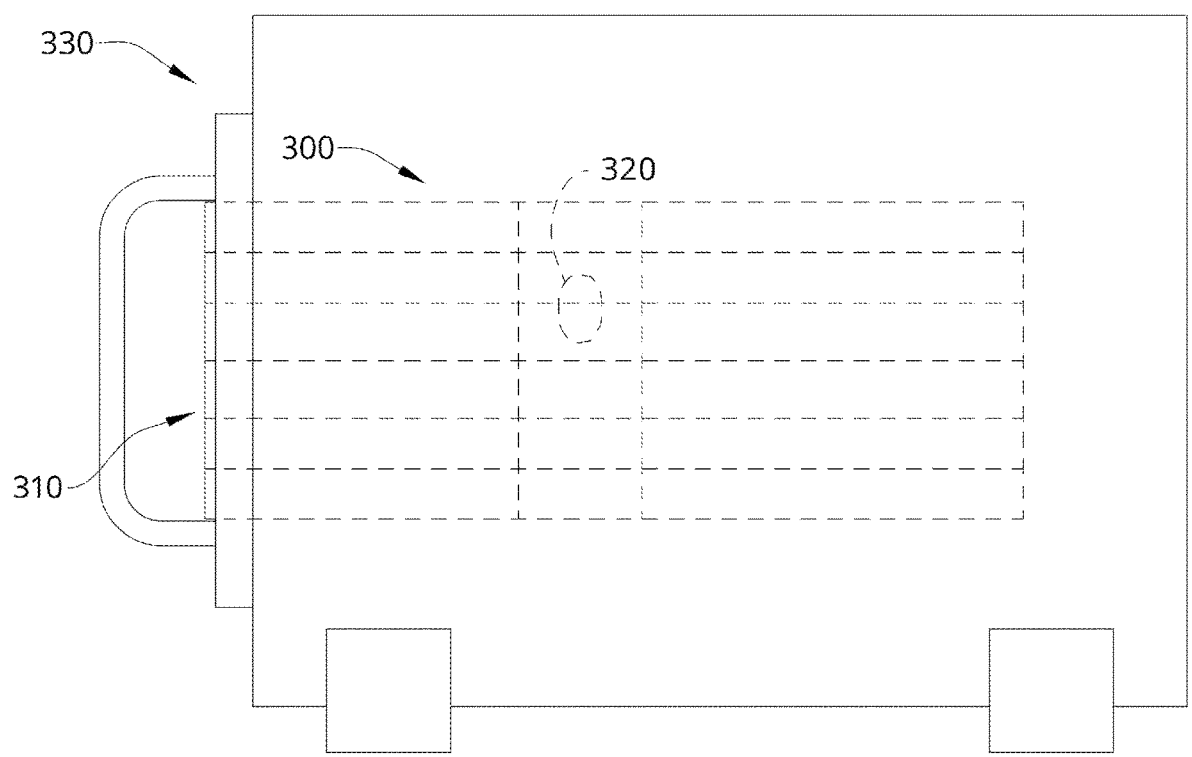
FIG. 10 conceptually illustrates a side view of the tumor tracking block as placed in the ArcCheck phantom system in some embodiments.

By way of example, FIGS. 9-10 conceptually illustrate application of a tumor tracking block in an ArcCheck phantom system. Specifically, FIG. 9 conceptually illustrates a perspective view of a tumor tracking block placed in an ArcCheck phantom system, while FIG. 10 conceptually illustrates a side view of the tumor tracking block as placed in the ArcCheck phantom system.

As shown in these figures, a tumor tracking block 300 is formed by long, rectangular blocks 310 that slide into a cavity of the ArcCheck phantom 300 through the front. The rectangular blocks 310 are joined together when inserted into the cavity of the ArcCheck phantom 300, thereby forming the tumor tracking block 300 for use with the ArcCheck phantom 300. In particular, the rectangular blocks 310 are similar to rectangles 110-140 that are joined together to form the tumor tracking block 100, described above, by reference to FIGS. 1-8. Specifically, the rectangular blocks 310 may variously have carved out portions which, when joined together with other rectangular blocks 310, form inner chambers of the tumor tracking block 300. Those inner chambers may be filled with liquid-formed epoxy of various densities, to form target objects which ultimately vary in size, shape, position, and/or density within the tumor tracking block 300. In this figure, a target object 320 is shown spanning at least a couple of the rectangular blocks 310. Other rectangular blocks 310 may or may not have inner chambers with target objects. While not shown in this figure, some of the rectangular blocks 310 include metal fiducial markers, such as those described above, by reference to FIGS. 2-6. The fiducials would be added to the tumor tracking block 300 and used by the LINAC to mark tumors in human (or animal) treatment.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

I claim:

1. A tumor tracking block comprising:
   a plastic block of a size configured to fit into slotted area spatial dimensions of a dock of a dynamic radiation oncological phantom system;
   an inner non-symmetric shaped chamber at a first location within the plastic block;
   a non-symmetric shaped target object within the inner non-symmetric shaped chamber, wherein the non-symmetric shaped target object comprises a liquid-formed epoxy volume; and
   a plurality of metal fiducial markers within the plastic block and used by a medical linear accelerator (LINAC) to mark tumors in human treatment when the plastic block is positioned in the dock of the dynamic radiation oncological phantom system to track treatment delivery to the non-symmetric shaped target object by the LINAC.

2. The tumor tracking block of claim 1, wherein the liquid-formed epoxy volume forms the non-symmetric shaped target object when liquid epoxy is filled within the inner non-symmetric shaped chamber, wherein the non-symmetric shaped target object further comprises a particular metal fiducial marker within the liquid-formed epoxy volume that is filled into the inner non-symmetric shaped chamber.

3. The tumor tracking block of claim 1 further comprising:
   a second inner chamber at a second location within the plastic block, wherein the second location is different from the first location; and
   a second target object within the second inner chamber.

4. The tumor tracking block of claim 3, wherein the second target object has a second density that is different from a first density of the non-symmetric shaped target object.

5. The tumor tracking block of claim 3, wherein the second target object has a second size that is different from a first size of the non-symmetric shaped target object.

6. The tumor tracking block of claim 3, wherein the second target object has a second shape that is different from the shape of the non-symmetric shaped target object.

7. The tumor tracking block of claim 1, wherein the plastic block comprises a plurality of plexiglass rectangles that are joined together to form the plastic block.

8. The tumor tracking block of claim 7, wherein the inner non-symmetric shaped chamber at the first location within the plastic block is carved out of a first side of a first plexiglass rectangle and a second side of a second plexiglass rectangle in the plurality of plexiglass rectangles, wherein the first side of the first plexiglass rectangle is joined with the second side of the second plexiglass rectangle to form a junction, wherein the inner non-symmetric shaped chamber spans the junction between the first plexiglass rectangle and the second plexiglass rectangle when the first plexiglass rectangle and the second plexiglass rectangle are joined together to form the plastic block.

* * * * *